(12) United States Patent
Mehus et al.

(10) Patent No.: US 7,543,761 B2
(45) Date of Patent: Jun. 9, 2009

(54) METHOD AND APPARATUS FOR DISPENSING FRAGRANCES

(75) Inventors: Richard Jondall Mehus, Richfield, MN (US); Charles Allen Hodge, Cottage Grove, MN (US)

(73) Assignee: Ecolab Inc., Saint Paul, MN (US)

( * ) Notice: Subject to any disclaimer, the term of this patent is extended or adjusted under 35 U.S.C. 154(b) by 709 days.

(21) Appl. No.: 11/184,340

(22) Filed: Jul. 19, 2005

(65) Prior Publication Data

US 2007/0018010 A1   Jan. 25, 2007

(51) Int. Cl.
*A62C 5/02* (2006.01)
*A62C 13/62* (2006.01)
*A62C 13/66* (2006.01)
*A62C 31/00* (2006.01)
*A01G 27/00* (2006.01)

(52) U.S. Cl. ............... 239/10; 239/69; 239/303; 239/305; 239/328

(58) Field of Classification Search ............ 239/6, 239/69, 303, 304, 305, 328, 10; 222/1, 504; 422/124; 454/337
See application file for complete search history.

(56) References Cited

U.S. PATENT DOCUMENTS

| | | | |
|---|---|---|---|
| 4,467,941 A * | 8/1984 | Du | .................. 222/1 |
| 5,011,632 A | 4/1991 | Hashimoto et al. | |
| 5,023,020 A | 6/1991 | Machida et al. | |
| 5,030,253 A * | 7/1991 | Tokuhiro et al. | ............. 95/216 |
| 5,087,273 A | 2/1992 | Ward | |
| 5,111,477 A | 5/1992 | Maloney et al. | |
| 5,174,967 A * | 12/1992 | Fukuhara | ................... 422/124 |
| 5,175,791 A | 12/1992 | Hsieh et al. | |
| 5,186,869 A | 2/1993 | Stumpf et al. | |
| 5,368,822 A | 11/1994 | McNeil | |
| 5,382,410 A | 1/1995 | Peltier | |
| 5,466,399 A | 11/1995 | Von Kempski et al. | |
| 5,690,720 A | 11/1997 | Spero | |
| 5,810,265 A | 9/1998 | Cornelius et al. | |
| 5,817,168 A | 10/1998 | Wheless | |
| 5,820,791 A | 10/1998 | Canale | |
| 5,924,597 A * | 7/1999 | Lynn | .............................. 222/1 |
| 6,165,419 A | 12/2000 | Bullock et al. | |
| 6,347,992 B1 | 2/2002 | Durbin et al. | |
| 6,494,778 B2 | 12/2002 | Kossak et al. | |
| 6,524,537 B1 | 2/2003 | Lee | |
| 6,554,203 B2 | 4/2003 | Hess et al. | |
| 6,558,250 B1 | 5/2003 | Paschke | |
| 6,602,463 B1 | 8/2003 | Ortner | |
| 6,722,529 B2 | 4/2004 | Ceppaluni et al. | |
| 6,766,651 B2 | 7/2004 | Dillenback | |

(Continued)

FOREIGN PATENT DOCUMENTS

DE    4018020 A    12/1990

(Continued)

*Primary Examiner*—Len Tran
*Assistant Examiner*—Ryan Reis
(74) *Attorney, Agent, or Firm*—Fredrikson & Byron, PA

(57) ABSTRACT

A method and apparatus dispenses first and second fragrances by utilizing a fog nozzle in a ductwork of a facility. The first fragrance is dispensed, at intervals, through the fog nozzle into the ductwork and the second fragrance is dispensed after the first fragrance is dispensed, wherein fragrance desensitivity is reduced.

11 Claims, 2 Drawing Sheets

U.S. PATENT DOCUMENTS

2003/0192959 A1 * 10/2003 Hess et al. .................... 239/69

FOREIGN PATENT DOCUMENTS

| DE | 4409598 A | 9/1995 |
|---|---|---|
| EP | 530081 A | 3/1993 |
| EP | 1033140 A2 | 9/2000 |
| EP | 1252900 B1 | 5/2004 |
| FR | 2670568 A1 | 6/1992 |
| JP | 9308677 A | 12/1997 |
| JP | 2889614 B2 | 5/1999 |
| SU | 1539473 A | 1/1990 |
| WO | WO/0235131 A2 | 5/2002 |
| WO | WO/2004037299 A2 | 5/2004 |

* cited by examiner

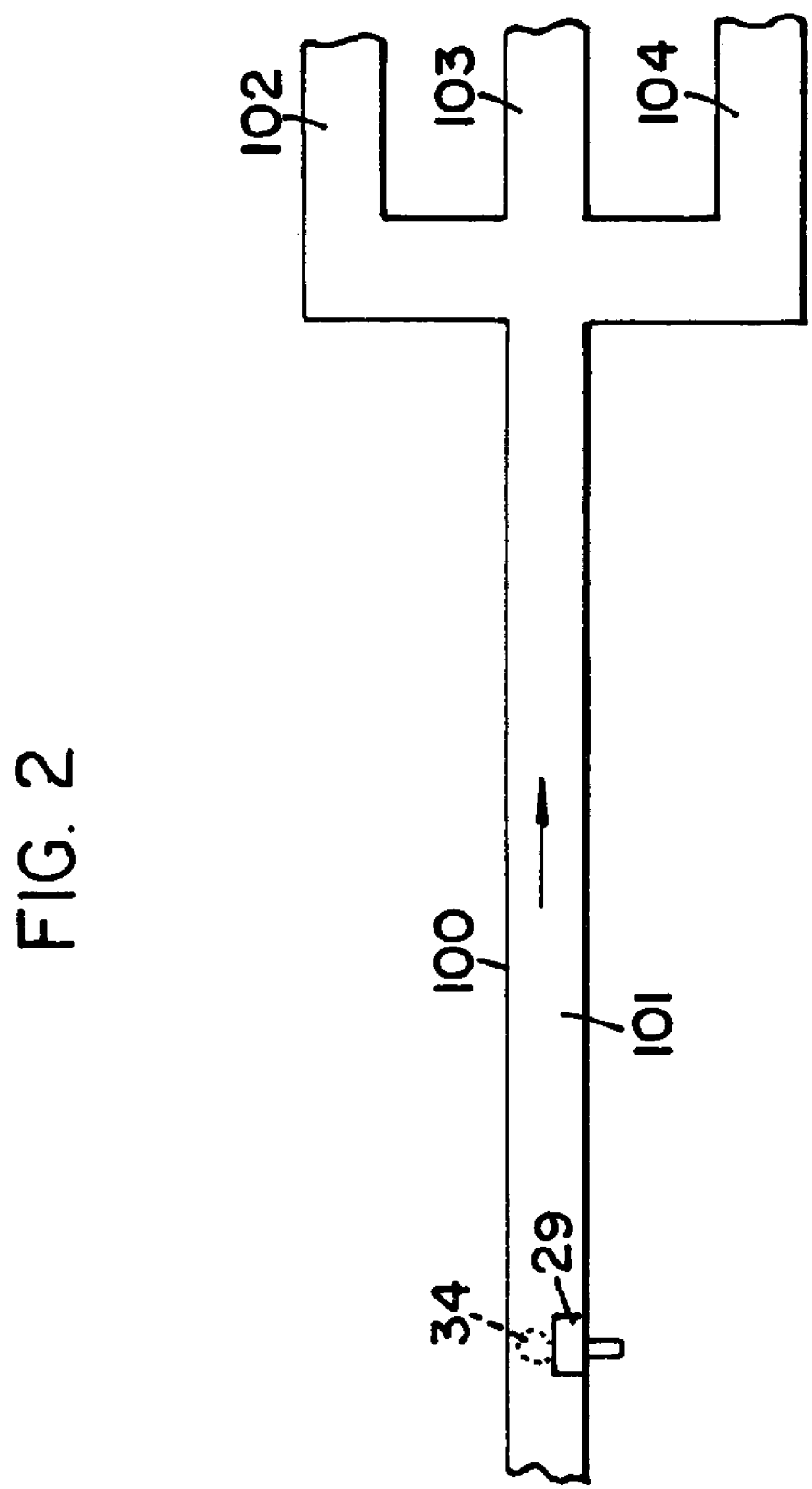

METHOD AND APPARATUS FOR DISPENSING FRAGRANCES

BACKGROUND OF THE INVENTION

1. Field of the Invention

This invention relates generally to the field of dispensing fragrances and more particularly to dispensing multiple fragrances to reduce fragrance desensitivity.

2. Description of the Prior Art

The dispensing of fragrances through HVAC ductwork is known. One example of this is U.S. Pat. No. 5,924,597. In that patent, multiple fragrances are dispensed and each fragrance container is controlled by a separate solenoid. While various fragrances may be dispensed, the same fragrance is dispensed into an individual room.

If the same fragrance is used in a room, after a period of time, a person becomes desensitized to the fragrance. Therefore, the effectiveness of a fragrance is diminished over time.

For aroma therapy, there are apparatuses that do dispense different aromas to a single room. The aromas are changed depending upon the time of day or the desired effect that is hoped to be accomplished by the aroma therapy.

The present invention addresses the problems associated with the prior art and provides for a method and apparatus for dispensing fragrances to reduce fragrance desensitivity.

SUMMARY OF THE INVENTION

The present invention is a method of dispensing first and second fragrances. The method includes positioning a fog nozzle in a ductwork of a facility. The first fragrance is dispensed, at intervals, through the fog nozzle into the ductwork. After dispensing the first fragrance, there is a switchover to dispensing, at intervals, the second fragrance into the ductwork, wherein fragrance desensitivity is reduced.

In another embodiment, the invention is a method of dispensing a first fragrance from a first sealed flexible pouch and a second fragrance from a second sealed flexible pouch. The pouches are in fluid communication with a vacuum selection switch. The vacuum selection switch is in fluid communication with a fog nozzle. The method includes positioning a fog nozzle in a ductwork of a facility. The vacuum selection switch is set to allow flow of the first fragrance. The first fragrance is dispensed, at intervals, through the fog nozzle into the ductwork. The vacuum selection switch is switched, by the first sealed flexible pouch creating a vacuum to be emptied, to allow flow of the second fragrance. The second fragrance is dispensed, at intervals, through the fog nozzle into the ductwork, wherein fragrance desensitivity is reduced.

In another embodiment, the invention is an apparatus for dispensing fragrance. The apparatus includes a first fragrance sealed in a first flexible pouch and a second fragrance sealed in a second flexible pouch. A vacuum selection switch is in fluid communication with the first fragrance and the second fragrance. An aspirator has product inlet in fluid communication with the vacuum selection switch, a water inlet adapted to be connected to a source of pressurized water, and a solution outlet in fluid communication with a fragrance solution container. A fog nozzle is in fluid communication with the fragrance solution container, the fog nozzle adapted and configured to be positioned proximate ductwork of a facility. A source of pressurized air is operatively connected to the fog nozzle and a controller is utilized for controlling when the source of pressurized air is delivered to the fog nozzle.

BRIEF DESCRIPTION OF THE DRAWINGS

FIG. 2 is a schematic view of the apparatus shown in FIG. 1 installed in a ductwork of a facility.

DETAILED DESCRIPTION OF THE EMBODIMENTS

Figure 1:
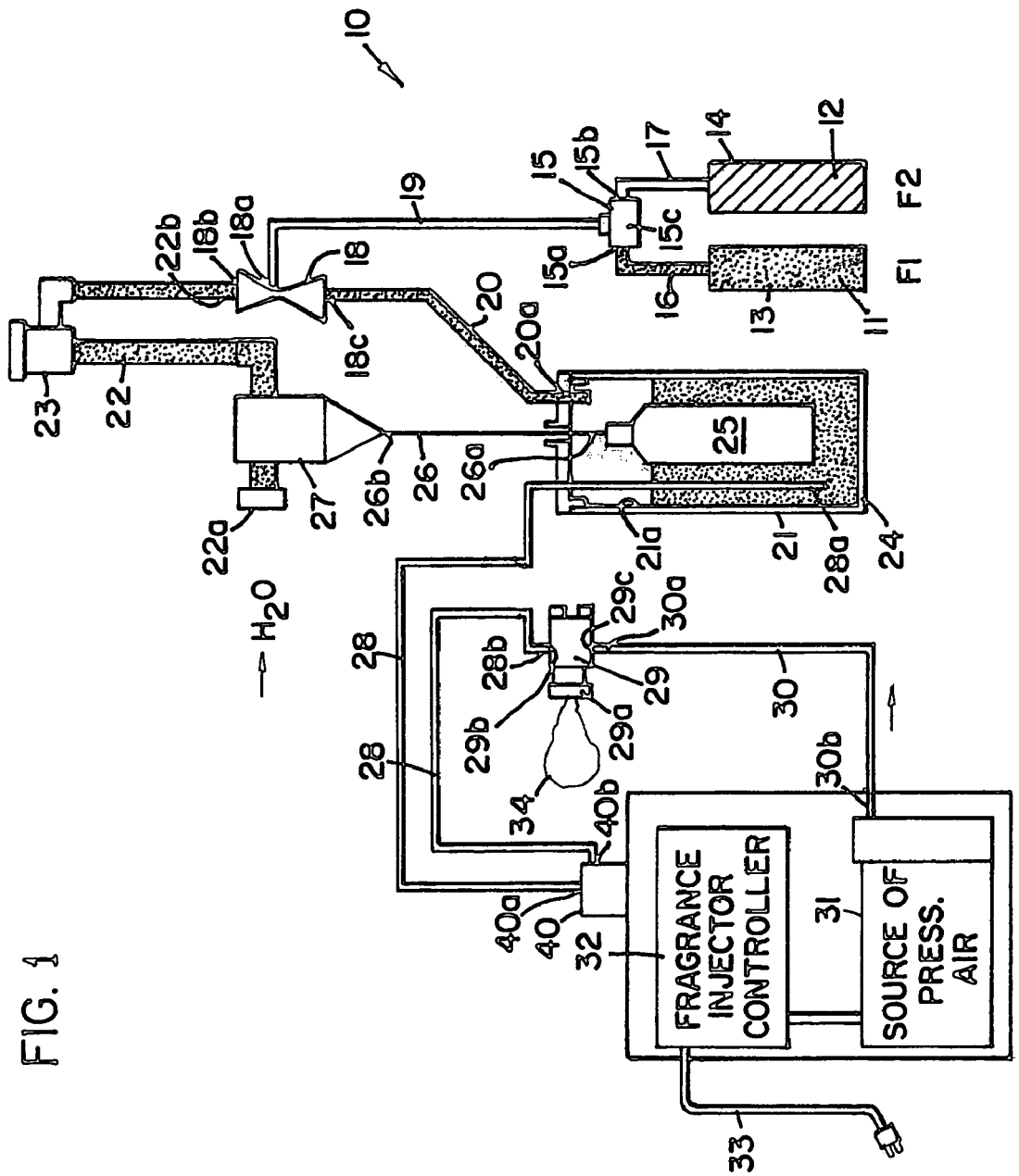
FIG. 1 is a schematic view of the apparatus of the present invention.

Referring to the Drawings, wherein like numerals represent like parts throughout the several views, there is generally disclosed at 10 a fragrance dispenser. The fragrance dispensed can be any suitable fragrance. The fragrance dispenser 10 utilizes at least two fragrances, 11 and 12. The fragrances 11 and 12 are liquids and are in a flexible pouch 13, 14 respectively. The pouches 13, 14 have a suitable connection such as a spout to allow access into the pouches 13 and 14. One suitable spout would be a CLEAN CLIC SYSTEM™ by Innovative Packaging Network (Itasca, Nev.), which is disclosed in U.S. Pat. No. 6,126,045, incorporated by reference herein.

A vacuum selector switch 15 is in fluid communication with both of the pouches 13, 14. A first conduit 16 is in fluid communication with the fragrance 11 in the first pouch 13 and a second conduit 17 places the vacuum selection switch 15 in fluid communication with the fragrance 12. The vacuum selection switch 15 is a switch that will move from a first position to a second position when a vacuum is created at one of its inlets. The vacuum switch 15 has a first inlet 15a to which the first conduit 16 is connected and a second inlet 15b to which the second conduit 17 is connected. There is also a selector switch 15c which initially selects and allows passage of fluid through one of the inlets 15a or 15b. As will be more fully described hereafter, as the first fragrance 11 is used, a vacuum is created in the pouch 13 and, when the pouch 13 is empty, the vacuum is sufficient enough to activate the vacuum selection switch 15 to move to a second position where fluid flow through the second conduit 17 is allowed. This provides for an automatic switchover from the first pouch 13 to the second pouch 14 when the first pouch 13 is empty. An example of a suitable vacuum selection switch is Model 1500-030 FloJet Transfer Valve sold by FloJet Corporation of Foothill Ranch, Calif. The vacuum selection switch 15 is in fluid communication with an aspirator 18 by suitable means such as a conduit 19. The aspirator 18 has a product inlet 18a. The conduit 19 terminates at the product inlet 18a and a suitable metering tip may be utilized there. The aspirator 18 has a water inlet 18b and a solution outlet 18c. The solution outlet 18c is in fluid communication, via a suitable means such as conduit 20, with a fragrance solution container 21. A conduit 22 has a first end 22a that is adapted and configured to be connected to a source of pressurized water. A second end 22b is adapted and configured to be connected to the water inlet 18b of the aspirator 18. The use of an aspirator 18 is well known in the dispensing art and a suitable aspirator may be utilized. An anti-siphon valve 23 may be placed in the conduit 22 at a position well known in the art. As will be discussed more fully hereafter, either the liquid fragrance 11 or 12 is combined with the pressurized water by the aspirator 18 and a use solution 24, which is the diluted fragrance concentrate from fragrances 11 or 12 and is delivered to the fragrance solution container 21. Typically, the fragrance use solution 24 is approximately 10% of the fragrance concentrate and 90% water, although it is understood that other dilution ratios may also be utilized.

The fragrance solution container 21 is preferably an enclosed container for receiving the fragrance use solution 24 and has a cavity 21a in which the fragrance use solution 24 is stored. In addition, there is preferably a float 25 that will rise and fall in height in the fragrance solution container 21, depending upon the amount of fragrance use solution 24 in the container 21. A connecting rod, or other suitable connecting device 26, is attached at one end of the float 25. The other end 26b is operatively connected to a water valve 27. The water valve 27 is placed in the flow of the conduit 22 and controls water flow through the conduit 22. The water valve 27 is a type well-known in the art. As the float 25 rises, the water valve 27 will be moved to an off position, thereby stopping the flow of water through the conduit 22. When the fragrance use solution 24 drops in level in the container 21, the float 25 will move downward, thereby turning the water valve 27 to a second position that allows the water to flow and more use solution 24 is created from the fragrance 12 or 13 and the water.

The conduit 20 has a first end 20a that is positioned through an opening in the top of the container 21. Preferably, this is a fit that does not allow fragrance to exit the container 21. Similarly, the rod 26 extends through an opening in the container 21. This opening is also preferably designed to minimize any escape of the vapors of the fragrance use solution 24. Finally, there is an opening through which a pickup tube 28 is positioned. One end 28a of the pickup tube 28 extends to proximate the bottom of the container 21. The pickup tube exits through an opening in the container 21, that is again preferably constructed so that no vapors from the fragrance use solution 24 escape. The pickup tube 28 has a second end 28b that is in fluid communication with an atomizer 29. A pump 40 has an inlet 40a into which the pickup tube 28 is in fluid communication and an outlet 40b in which the second portion of the pickup tube 28 is in fluid communication. The second portion of the pickup tube 28 terminates with the second end 28b. A pump 40 is utilized to deliver the fragrance use solution to the atomizer 29. The pump 40 may be located in any suitable place such as by being positioned proximate the controller 32.

The atomizer 29 includes a nozzle 29a. The nozzle 29a has a first inlet 29b in fluid communication with the conduit 28 and a second inlet 29c in fluid communication with a first end 30a of an air conduit 30. The second end 30b of the conduit 30 is operatively connected to a source of pressurized air such as an air compressor 31. A fragrance injector controller 32 is utilized for controlling the operation of the air compressor 31, and thereby the dispensing of the fragrance 12 or 13, as will be disclosed more fully hereafter. One suitable controller would be a seven-day/24-hour programmable controller that allows for active times of the week and day. Typically, the on/off times will be from 30-90 seconds every 15-20 minutes for portions of a day or for the entire 24-hour period. A power cord 33 is shown and is utilized to provide power to the controller 32 and the air compressor 31.

The nozzle 29a is preferably a nozzle that provides a particle diameter wherein at least half and preferably at least three-fourths of the particles are five microns or less. This results in a fog or mist that is more easily dispersed throughout the ductwork of a facility. One suitable nozzle is model 1/4JH+SU (nickel plated brass using a 1650 nozzle and Air Cap-64) sold by Spraying Systems Co. of Wheaton, Ill.

FIG. 2 is a schematic representation of a ductwork 100 in a building or facility. The ductwork 100 has a central duct 101 in which the fragrance dispenser 10 is positioned. In FIG. 2 only the atomizer 29 is shown. The ductwork 100 is shown as having three separate branches 102-104. However, it is understood that there may be only the central duct 101 and more or less than three branches. The central HVAC system for the facility will provide for a flow of air in the direction of the arrow shown in FIG. 2.

In use, the flexible pouch 13 and flexible pouch 14 containing fragrances 11, 12 are connected to the vacuum selection switch 15. The vacuum selection switch 15 is moved to a position to allow flow from one of the pouches, such as pouch 13. Water pressure is then supplied to the conduit 22 and depending upon the position of the valve 27, water will either flow or not flow through to the aspirator 18. If the float 25 is in a lower first position, the valve 27 will be on and will allow water to flow through the conduit 22 through to the aspirator 18. At that time, the fragrance 11 will be drawn up through the conduit 16, through the vacuum switch 15, the conduit 19 and mixed with the water to form a use solution 24 that exits the aspirator 18 and is dispensed into the fragrance solution container 21. This will eventually cause the float 25 to rise and turn off the water valve 27. As previously discussed, the controller 32 may be any suitable controller and provide for control either for portions of a day or for the entire day. Further, the controller can be set to change the length of time that it is on, typically from 30-90 seconds and the frequency such as every 15-20 minutes. When the controller is on, the controller energizes the air compressor 31 and the pump 40. The pump 40 draws the fragrance solution 24 to the atomizer 29, where the fragrance use solution 24 is atomized by the atomizer 29 and the pressurized air and dispensed in a fog or mist 34. As the fragrance 11 is dispensed from the flexible pouch 13, the float 25 will automatically refill the fragrance solution container 21. Over repeated cycles, the product flexible pouch 13 will be empty. The vacuum from the aspirator 18, when filling the fragrance solution container 21, will switch the pickup from the empty pouch 13 to the full pouch 14. If different, but compatible fragrance concentrates are used in the pouches 13, 14, when switching from the empty pouch to a full pouch, a new fragrance can be introduced into the ductwork 100 of a building or facility. The fog or mist 34 dispensed in the ductwork 100 is then carried by the movement of the HVAC system and is dispersed throughout the room. Since people often become desensitized to a fragrance after a period of time, the automatic switching over to a second fragrance will prevent the fragrance desensitivity that is accompanied by the constant dispensing of only a single fragrance. Then, while the second pouch is being dispensed, the first, empty pouch may be removed and replaced.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of dispensing first and second fragrances, comprising:
    (a) positioning a fog nozzle in a ductwork of a facility;
    (b) connecting a conduit to a source of pressurized water;
    (c) turning on a water valve, to supply water pressure, from the source, in order to draw the first fragrance through the conduit, where the first fragrance mixes with water to form a first fragrance solution;
    (d) dispensing, at intervals, the first fragrance solution through the fog nozzle into the ductwork;
    (e) after dispensing the first fragrance solution, drawing the second fragrance through the conduit, where the second fragrance mixes with water to form a second fragrance solution; and (f) dispensing, at intervals, the second fragrance solution into the ductwork.

2. The method of claim 1, wherein a fog from the fog nozzle contains particles and at least ½ of the particles have a size of 5 microns or less.

3. The method of claim 2, wherein at least ¾ of the particles have a size of 5 microns or less.

4. A method of dispensing a first fragrance from a first sealed flexible pouch and a second fragrance from a second sealed flexible pouch, the pouches in fluid communication with a vacuum selection switch, the vacuum selection switch in fluid communication with a fog nozzle, the method comprising:
(a) positioning a fog nozzle in a ductwork of a facility;
(b) selling the vacuum selection switch to allow flow of the first fragrance from the first pouch;
(c) dispensing, at predetermined intervals, the first fragrance through the fog nozzle into the ductwork; and
(d) dispensing, at the predetermined intervals, the second fragrance, from the second pouch, through the fog nozzle into the ductwork, after dispensing the first fragrance, and after the flow of the first fragrance from the first pouch empties the first pouch to create a vacuum that switches the vacuum selection switch, to allow flow of the second fragrance from the second pouch, wherein fragrance desensitivity is reduced.

5. The method of claim 4, wherein a fog from the fog nozzle contains particles and at least ½ of the particles have a size of 5 microns or less.

6. The method of claim 4, wherein at least ¾ of the particles have a size of 5 microns or less.

7. An apparatus for dispensing fragrance, comprising:
(a) a first fragrance sealed in a first flexible pouch;
(b) a second fragrance sealed in a second flexible pouch;
(c) a vacuum selection switch in fluid communication with the first fragrance and the second fragrance;
(d) an aspirator having a product inlet in fluid communication with the vacuum selection switch, a water inlet adapted to be connected to a source of pressurized water, and a solution outlet in fluid communication with a fragrance solution container;
(e) a fog nozzle in fluid communication with the fragrance solution container, the fog nozzle adapted and configured to be positioned proximate ductwork of a facility;
(f) a source of pressurized air operatively connected to the fog nozzle; and
(g) a controller for controlling when the source of pressurized air is delivered to the fog nozzle.

8. The apparatus of claim 7, further comprising:
(a) a valve positioned for controlling flow of water from the source of pressurized water; and
(b) a float positioned in the fragrance solution container, the float operatively connected to the valve and movement of the float turns the valve on and off.

9. The method of claim 1, further comprising:
setting a switch to select the first fragrance prior to drawing the first fragrance into the conduit; and
re-setting the switch to select the second fragrance, after dispensing the first fragrance solution and prior to drawing the second fragrance into the conduit.

10. The method of claim 9, wherein:
the first and second fragrances are contained in respective first and second sealed and flexible pouches, the pouches being in fluid communication with the switch;
the switch comprises a vacuum selection switch; and
re-setting the switch to select the second fragrance comprises drawing the selected first fragrance, through the conduit, until the first pouch is emptied to create a vacuum.

11. The method of claim 1, further comprising storing the first fragrance solution in a container, prior to dispensing the first fragrance solution; wherein the container includes a float adapted to turn off and on the water valve.

* * * * *

UNITED STATES PATENT AND TRADEMARK OFFICE
CERTIFICATE OF CORRECTION

PATENT NO. : 7,543,761 B2
APPLICATION NO. : 11/184340
DATED : June 9, 2009
INVENTOR(S) : Richard Jondall Mehus et al.

It is certified that error appears in the above-identified patent and that said Letters Patent is hereby corrected as shown below:

Column 5
Line 15, "selling" should read "setting".

Signed and Sealed this

Twenty-fifth Day of August, 2009

David J. Kappos
*Director of the United States Patent and Trademark Office*